United States Patent [19]

Kuehl

[11] 4,420,690
[45] Dec. 13, 1983

[54] SPECTROMETRIC MICROSAMPLING GAS CELLS

[75] Inventor: Donald Kuehl, Winchester, Mass.

[73] Assignee: Bio-Rad Laboratories, Inc., Richmond, Calif.

[21] Appl. No.: 354,933

[22] Filed: Mar. 5, 1982

[51] Int. Cl.³ .................... G01N 21/00; G01N 23/10
[52] U.S. Cl. .................................................. 250/428
[58] Field of Search ............... 250/428, 432 R, 435, 250/437, 343, 373

[56] References Cited

PUBLICATIONS

Turnbull, M. S., "Non-Dispersive Infra-Red Gas Analyzers." *Electronics and Instrumentation*, vol. 2, No. 12, (Mar. 1972), pp. 11–15.

Saperstein, David D. "Analysis of the Gaseous Components of Reactions by Fourier Transform Infrared Spectrometry" *Analytical Chemistry*, vol. 52, No. 11 (Sep. 1980), pp. 1565–1570.

*Primary Examiner*—Alfred E. Smith
*Assistant Examiner*—C. Hannaher
*Attorney, Agent, or Firm*—Schiller & Pandiscio

[57] ABSTRACT

A sample cell for absorption spectrometry of small volume samples in a continuously flowing carrier gas stream is in the form of an elongate small-bore hollow tube with optically transparent end windows -sealed to the tube and held so as to axially captivate the tube within a through-bore in a rigid, thermally conducting, holder. Radial openings through the tube proximate the window seal, together with matching bores in the holder, are provided to accommodate fluid transfer lines. The transfer lines are resiliently sealed to tube and holder to permit differential expansion between tube and holder.

7 Claims, 2 Drawing Figures

SPECTROMETRIC MICROSAMPLING GAS CELLS

FIELD OF THE INVENTION

This invention relates to gas sampling cells for use in absorption spectrometry, and more particularly to such cells useful in the real-time infrared assay of individual output peaks obtained from a continuously flowing capillary gas chromatograph.

BACKGROUND OF THE INVENTION

Infrared absorption spectrometry is a well-known technique for the assay of materials, and its use in combination with other analytical techniques is widely practiced. A combined assay finding wide application is the spectrometric assay of the constituents of a mixture, the mixture having first been divided into its constituent parts by gas chromatography.

While in principle the various fractions of a mixture separated by gas chromatography could be individually trapped (and concentrated) for subsequent spectrometric analysis, such a procedure is often inconvenient. Alternative approaches include slowing down or intermittently stopping the flow through the chromatographic column sufficiently to allow a fraction to be observed spectrometrically. Either of these alternative approaches is also frequently inconvenient, and further, leads to degraded chromatographic resolution (this last disadvantage is particularly true in the case of intermittently stopping the flow through the column).

Another approach, and one which is finding increasing application, is to make the spectrometric observations of the fractions "on the fly" as each fraction is eluted from the column at the normal carrier gas velocity. In this approach, the gas flowing from the chromatographic column is made to flow continuously through an optical cell forming a portion of the optical path of an illumination source/spectrometer system. The exhaust from the optical cell may in turn be throttled to atmosphere or conveyed to a further analysis station, as, for instance, a flame ionization detector or a mass spectrograph. It is with regard to such apparatus that the present invention is concerned.

It will be appreciated that the optical cell used for "on the fly" analysis must not only be matached to the optical requirements of the spectrometer, but to the flow requirements of the chromatograph (and any subsequent detectors) as well. The optical cell should present sufficient optical path length through the sample to insure adequate optical absorption and further be throughput-matched to the aperture and field of view of the source/spectrometer optical system. Chromatographically, the cell should not materially affect the flow rate of the chromatograph nor be a source of leakage or dead volume to any subsequent detectors.

The optical requirements for long path length and throughput matching of a cell delimiting a flowing stream have been met in prior art devices by flowing the sample through an elongate hollow tube with transparent ends, and observing the sample along the axis of the tube, the tube functioning as a light pipe. The desireable long path length is provided by the length of the tube, while multiple reflections from the interiorwalls of the tube act to preserve the system's optical throughput. For infrared spectrometry, as is commonly employed in such applications, the tube may be fabricated of any of a number of materials, and its inner surface made highly reflective as, for instance, by a gold coating. The windows of such cells must be highly transparent in the spectral region of interest, and, for the infrared, are often polished plates of sodium chloride. This latter material is both water soluble and easily damaged mechanically, and consequently such cells are fabricated with removable end windows, the mounting of the windows both sealing the cell and providing for differential expansion of the component parts of the cell. Typically, the end-window mounting also incorporates the couplings for the fluid transfer lines between the chromatograph and the cell and between the cell and subsequent devices.

Such sample cells have been successfully used for spectrometric assays of the effluent from normal gas chromatographic systems, where the sample size is sufficient to minimize the effect of the small dead volume inherent in the tube interior between windows. The situation is complicated in the case of capillary chromatography, however, where the sample is typically less than $10^{-7}$ gram and where concentrations of each of the eluted fractions are on the order of $10^{-8}$ g/ml. For such small samples and low fraction concentrations, leakage and dead volume are critical factors. From a spectrometric standpoint, the dead volume of prior art light-pipe flow cells is a significant percentage of the small size of the eluted sample fraction. Consequently, for such samples in such optical cells, spectrometric detection and chromatographic resolution are seriously degraded. The situation is further exacerbated by the short dwell time of an eluted fraction in the optical cell. While the outlet flow rate of a typical capillary column is generally on the order of 1 cc/min., the linear flow rate is considerable, due to the small bore (0.2–0.5 mm) of the column.

Additionally, the small sample size makes contamination or absorption of the sample by seals and the like a serious source of potential error.

An approach that has been employed to compensate in part for the optically non-observed dead volume in prior art optical cells has been to inject additional carrier gas into the stream flowing into the cell, thereby diluting the eluted fraction and making possible an overall larger volume cell with a correspondingly smaller percentage dead volume. However, this approach is not without its own disadvantages. While the increased cell volume permits a greater-length optical path, the length gain is offset by the dilution of the sample. Further, the maintenance of optical throughput in a longer cell requires more reflections from the cell wall, with a consequent loss in cell transmission and optical performance. It will also be recognized that the dilution of the fraction will adversely affect the performance of any concentration sensitive systems following the optical cell. Additionally, this approach does not address the problem of contamination or loss of sample through interaction with the various seals and packings used to secure the transfer lines, the windows, and the light pipe to one another.

Accordingly, it is an object of the present invention to provide an optical cell for the spectrometric analysis of small fluid samples having a minimum dead volume.

It is also an object of the present invention to provide such an optical cell which is particularly suited for "on the fly" analysis of fractions eluted from a capillary gas chromatography.

It is a further object of the present invention to provide such an optical cell which does not require the further dilution of an eluted fraction.

Yet again, it is an object of the present invention to provide an optical cell wherein the effects of the interaction between seals, packings, and sample are minimized.

BRIEF DESCRIPTION OF THE INVENTION

These and other objects are met in the present invention of a sample cell for absorption spectrometry of small volume samples in a continuously flowing carrier gas stream, which cell, in a preferred embodiment, is in the form of an elongate small-bore hollow tube with optically transparent end windows sealed to the tube so as to resiliently captivate the tube within a through-bore in a rigid, thermally conductive holder. Radial passageways through the tube proximate the window seal, together with matching bores in the holder, are provided to accommodate flexible, capillary, fluid-transfer lines. The transfer lines are resiliently sealed to tube and holder, thereby permitting differential expansion between tube and holder without endangering transfer lines or system integrity.

Unlike prior art light-pipe sample cells, the coupling to the transfer line is made through the walls of the light pipe, and the windows are more intimately sealed to the ends of the light pipe near these couplings. It will be appreciated that the present invention thus minimizes the ratio of the dead volume (presented by fluid transfer line couplings and window mountings) to cell volume. By the same token, the present invention also minimizes exposure of the sample stream to seals and packings, thereby reducing danger of sample contamination or loss.

The minimal size of the dead volume obviates the need for dilution of the eluted fraction, making the system particularly suitable for use with capillary chromatographic - spectrometic systems used in conjunction with other detectors.

Other objects of the present invention will in part appear obvious and will in part appear hereinafter. The invention accordingly comprises the apparatus possessing the construction, combination of elements, and arrangement of parts which are exemplified in the following detailed disclosure, and the scope of the application of which will be indicated in the claims.

BRIEF DESCRIPTION OF THE DRAWINGS

For a fuller understanding of the nature and objects of the present invention, reference should be had to the following detailed description taken in connection with the following drawings wherein.

In the two views, like index numbers refer to like components.

DETAILED DESCRIPTION OF THE DRAWINGS

Figure 1:
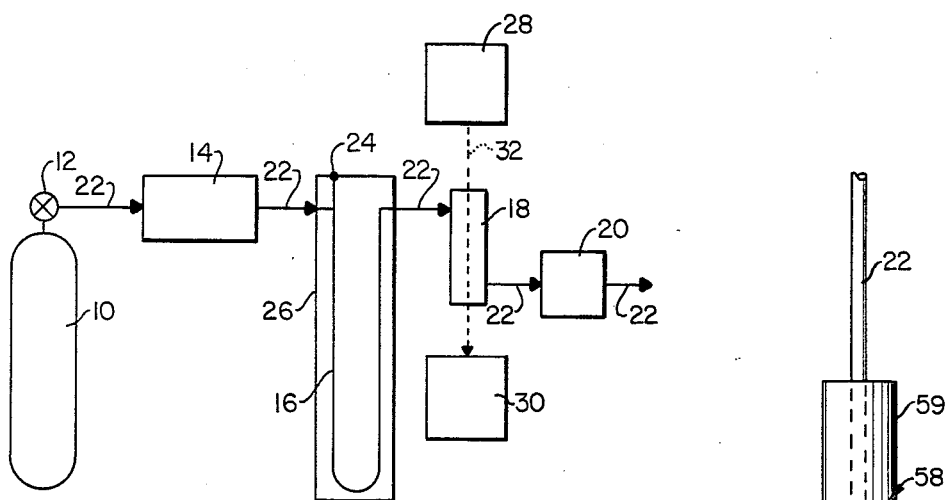
FIG. 1 is a schematic diagram of a gas chromatographic system which may be used in conjunction with the sample cell of the present invention.

Referring to FIG. 1, there may be seen an exemplary schematic diagram of a gas chromatographic infrared (GCIR) system such as would incorporate the present invention. The GCIR system comprises gas supply 10, flow regulator 12, flow monitor 14, chromatographic column 16, sample cell 18, and detector 20, all connected to one another seriatim in that order by fluid conductive transfer line 22. In the realization of the present invention, it has been found that polyimide-coated fused silica capillary tubing is particularly suitable as the transfer line between sample cell 18 and adjacent components of the system, although it will be recognized that other types of transfer line may also be used.

As is well known in the art, a sample to be analyzed is injected, typically by a syringe (not shown) through sample injection port 24 (typically a septum) at one end of column 16, where it mixes with and is propelled through the system by the flow of a carrier gas. For the small samples typical of capillary chromatography, sample injection port is typically supplied with a stream splitter (not shown) that divides the stream of mixed sample and carrier gas into a pair of streams of fixed size ratio, the smaller stream being that supplied to the input end of the chromatographic column. The sample, driven by the flow of a carrier gas (for instance, helium, nitrogen, argon, or the like) from gas supply 10, is forced through column 16, the various constituents of the sample traveling through the column at different rates as a result of differing physical properties, the constituents being differently sorbed to the stationary phase on the column's wall. Column 16 is typically enclosed in an oven 26 in order that its temperature may be controlled.

Spectrometric analysis is performed by observing the attenuation of a beam of radiation (i.e., for GCIR analysis, infrared radiation, although for other purposes, visible or other radiation might be used) passed through the sample in sample cell 18. As will be described in detail hereinafter, sample cell 18 is in the form of an elongate hollow light pipe with optically transmissive end windows. The sample stream, introduced into this light pipe at one end and withdrawn at the other end, may be illuminated through one of the windows, as by scanning monochrometer 28, and observed through the other window, as by radiation detector 30, the output from monochrometer 28 being restricted to a cone coaxial with axis 32 of the sample cell 18. Alternatively, monochrometer 28 could be replaced by a spectrally broad band radiation source and radiation detector 30 incorporated into a scanning spectrometer. It also will be understood that for detailed spectrometric observations of rapidly moving samples monochrometer 28 and radiation detector 30 (or the spectrometer incorporating radiation detector 30) desireably form a multiplex system.

The sample flowing from sample cell 18 is passed on to detector 20, which may be, for instance, a flame ionization detector or a mass spectrometer.

Figure 2:
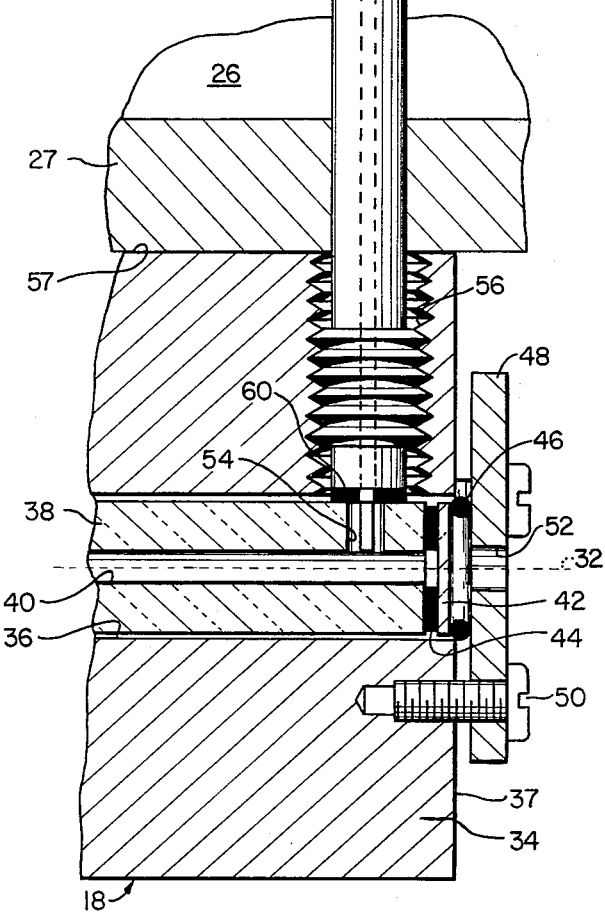
FIG. 2 is an enlarged fragmentary cross-sectional view of an end of a sample cell made in accordance with the present invention.

Turning now to FIG. 2, there may be seen in greater detail an end of sample cell 18 constituting the preferred embodiment of the present invention. Sample cell 18 has two similar ends, respectively facing monochrometer 28 and detector 30, and for brevity only one will be described in detail, it being understood the other end of sample cell 18 is substantially identical in structure.

Preferably, the main structure of sample cell 18 is cell body 34. Cell body 34 is an elongate block of material penetrated throughout by an elongate bore 36 of circular cross-section. The axis of bore 36 is preferably substantially normal to faces 37 of cell body 34 penetrated by the bore. Faces 37 are further preferably substantially planar. Bore 36 is dimensioned to accept an open-ended hollow tubular light pipe 38 which, as will be described hereinafter, is of slightly shorter length than the length of cell body 34. Cell body 34 is preferably fabricated from a material having a high thermal conductivity, typically a metal. The material of cell body 34 may also be chosen to have a similar coefficient of thermal expansion as that of light pipe 38 (e.g., for a fused silica light pipe 38, cell body 34 may be of nickel-iron alloy, such as invar or kovar steel). However, as will become apparent, the present invention incorporates provision for differential expansion of the cell body and the light pipe.

Light pipe 38 is typically a glass or fused silica right circular cylindrical hollow tube intended to propogate radiant energy through the hollow portion thereof. Preferably, but not necessarily, the interior wall of light pipe 38 is provided with a reflective coating 40. Reflective coating 40 is chosen to have high reflectivity in the spectral region of interest and further to be non-reactive to the material being assayed. For example, for infrared spectroscopy, reflective coating 40 may be of gold, chemically or otherwise deposited on the interior surface of the light pipe.

Each end of light pipe 38 is sealed with a window 42, in the form of a flat disk with a circular periphery, the disk being mounted concentrically about and with its flat surface normal to the axis of the light pipe. Each window 42 has a diameter substantially equal to the outside diameter of light pipe 38. Windows 42 are fabricated of a material chosen to be highly transmissive in the spectral region of interest and to be nonreactive to the material being assayed. Typically, windows 42 may be of glass, fused silica, salt, or other optical materials known in the art. A thin, washer-like seal 44 is sandwiched between the end of light pipe 38 and each window 42. Seal 44 is preferably a fluid-impervious, chemically inert, nonleachable material. Suitable materials for seals 44 include perfluoro elastomer (such as that manufactured by E. I. du Pont de Nemours & Co. under the trademark Kalrez) or a similar elastomer. Alternatively, seal 44 may be of graphite or rubber. Window 42 is compressably held in contact with seal 44, and the seal 44, with the end of light pipe 38, by an elastic ring such as rubber spring 46 and by washer 48. Washer 48 is secured to face 37 of cell body 34, as by a plurality of machine screws 50. The central aperature 52 of washer 48 is chosen to have a larger diameter than the inside diameter of light pipe 38, and washer 48 is disposed so that central aperture 52 is concentric with the axis of light pipe 38 and the center of window 42.

As may be seen by reference to FIG. 2, cell body 34 is dimensioned to exceed the length of light pipe 38 at each end of the latter by a distance on the order of the total combined thickness of seal 44 and window 42, but less than the total combined thickness of seal 44, window 42, and rubber spring 46. The assembly of light pipe, seal, window, and rubber spring is captivated in bore 36 by the associated washer 48, the washer clearing the respective face 37 of the cell body by a distance sufficient to permit the washer to be axially adjusted with respect to the light pipe in order to control the compression of rubber spring 46.

Disposed near each end of light pipe 38 is a radial bore 54. Each radial bore 54 penetrates throughout the wall of light pipe 38, communicating between the interior and exterior of the light pipe. The diameters of radial bore 54 are chosen to be between 1 and 3 times the outside diameter of transfer line 22, and each radial bore is spaced from the adjacent end of light pipe 38 by a distance on the order of the diameter of the radial bore. Satisfactory radial bores 54 have been formed in light pipes by such techniques as ultrasonic drilling; however, any suitable glass-working technique will suffice.

A pair of tapped bores 56 are disposed at each end of cell body 34. Each tapped bore 56 is colinear with a corresponding bore 54, so as to extend radially with respect to bore 36 and, in a preferred embodiment, is normal to face 57 (one of the faces orthogonal to faces 37) of cell body 18. Tapped bores 56 extend in the same direction from bore 36 and are spaced apart center-to-center a distance similar to the center-to-center spacing of radial bores 54. Each bore 56 is substantially equally spaced from the adjacent face 37 of cell body 34.

A thick-walled threaded fitting 58 dimensioned to accomodate transfer line 22 is provided for each tapped bore 56. Threaded fittings 58 preferably include an extension 59 which extends well beyond cell body 34 when fittings 58 are fully threaded into bores 56. The extent of extension 59 is chosen to be greater than the thickness of wall 27 of the oven 26 with which the optical cell is to be used. In order that a large surface area of the extension may be exposed to the interior of the oven. Fittings 58 are preferably of a material, such as copper, having a high thermal conductivity. In the preferred embodiment, each transfer line 22 communicating with optical cell 18 is inserted through the corresponding assembled fitting 58 (and bore 56) and the aligned bore 54 until the end of the transfer line is flush with reflective coating 40 on the inside of the light pipe. The transfer line is then cemented or otherwise sealed to the light pipe, as, for instance, with an elastomeric seal 60 of high-temperature gasket material between the light pipe and threaded fitting 58. The installation of transfer lines 22 through fittings 58 and bores 54 is facilitated by the relatively flexible nature of the polyimide coated fused silica capillary tubing preferably used for the transfer lines.

Preferably, sample cell 18 is incorporated into a system such that face 57 of cell body 34 is in thermal contact with wall 27 of oven 26, each threaded fitting 58 penetrating the wall of the oven to receive transfer lines 22 within the oven. In such an installation, tranfer lines 22 to and from sample cell 18 become external to oven 26 only within cell body 34. Fittings 58, due to their high thermal conductivity, place cell body 34 in thermal contact with the interior of oven 26. Wall 27 of oven 26 may also be uninsulated in the region of its contact with face 57 of cell body 34 in order to aid in the heat transfer. As a consequence, cell body 34 and light pipe 38 are heated to oven temperature, or nearly so. This, together with the high linear velocity of eluent through the portion of transfer lines 22 external to the oven and through light pipe 38, tends to minimize any temperature drop of the eluent while traversing the sample cell. It will be appreciated that, rather than being heated solely through contact with oven 26, transmission cell 18 might also include appropriate heaters of its own.

Inasmuch as radial bore 54 is of slightly larger diameter than transfer line 22, and light pipe 38 is captivated in bore 36 of cell body 34 by elastomeric seals 44 and 60 and by rubber spring 46, differential expansion between cell body 34 and light pipe 38 may be allowed for without damage to either light pipe 38 or transfer line 22. This particular mounting arrangement also allows for less stringent manufacturing tolerances and easier assembly.

The sample cell thus far described may be readily disassembled for the replacement or refiguring of windows 42 merely by removing screws 50, washer 40, and rubber spring 46. It will also be appreciated that sample cell 18 has a dead volume at each end of light pipe 38 on the order of the cube of the inside diameter of the light pipe. This is far smaller than the dead volume in those designs in which the fluid coupling is made into the window holder, for example as a part of cell body 34, the end of the light pipe being displaced from the window a sufficient distance to accommodate the transfer line coupling. It will also be appreciated that the only organic material exposed to the flow stream is the relatively small area of the inside diameter of seals 44 and the even smaller area of seals 60 surrounding the capillary transferlines and exposed through bores 54. Consequently, exposure of the sample to contamination, sorption, or reaction by or with the seals is minimized.

Those skilled in the art will readily recognize that various changes may be made in the apparatus herein described. Thus, for instance, windows 42 might be permanently sealed directly to the ends of light pipe 38 if the materials permit. Further, it will be recognized that radial bores 54 in light pipe 38 might be in the form of radial slots in the ends of the light pipe, thereby reducing further the dead volume of the optical cell. Yet again, it will be recognized that washers 48 could be held in compression against windows 42 by springs captivated to screws 50, the washers in turn directly contacting the windows without an intermediate rubber spring, the relative dimensions of cell body 34 and light pipe 38 being accordingly altered to permit contact between the windows and the washers. Then, too, it will be recognized that while a resilient bond, such as is provided by elastomeric seal 60, is preferred between tranferlines 22 and light pipe 38, the bond may be relatively rigid, particularly in the case where the coefficients of thermal expansion of light pipe and cell body 34 are substantially equal.

Since these and other changes may be made in the above apparatus without departing from the scope of the invention herein involved, it is intended that all matter contained in the above description or shown in the accompanying drawing shall be interpreted in an illustrative and not in a limiting sense.

What is claimed is:

1. A sample cell for absorption spectrometry of small volume samples in a continuously flowing carrier gas stream, said sample cell comprising in combination:
   a holder in the form of a body of thermally conductive material, said body having an elongate bore penetrating therethrough substantially normal to and between a first and a second face of said body, said body further being provided with a pair of secondary bores extending radially from said elongate bore and communicating therewith and with the exterior of said body, a one each of said secondary bores being located adjacent a respective one of said first and second faces;
   an elongate open-ended hollow tube dimensioned to fit said elongate bore and to extend therein substantially from said first face to said second face, said tube being further provided with a pair of radial openings communicating between the interior and the exterior of said tube and disposed substantially in axial alignment with said secondary bores;
   a pair of fluid conductive transfer line means, each of said transfer line means being disposed in fluid communication with the interior of said tube and the exterior of said body through a respective combined radial opening and secondary bore;
   means sealing and transferline means to said tube; and
   a pair of window means, each of said window means being secured to a respective one of said first and second faces and abutting and sealing a respective open end of said hollow tube.

2. A sample cell according to claim 1 wherein further said hollow tube is provided with a reflective interior surface.

3. A sample cell according to claim 2 wherein said reflective interior surface is of gold.

4. A sample cell according to claim 3 wherein further said window means are infrared transmissive windows.

5. A sample cell according to claim 1 wherein said radial openings are radial bores.

6. A sample cell according to claim 1 wherein further said holder and said hollow tube are fabricated of materials having substantially equal coefficients of thermal expansion.

7. A sample cell according to claim 6 wherein said holder is of invar or kovar and said hollow tube is of silica.

* * * * *

UNITED STATES PATENT AND TRADEMARK OFFICE
CERTIFICATE OF CORRECTION

PATENT NO. : 4,420,690

DATED : December 13, 1983

INVENTOR(S) : Donald Kuehl

It is certified that error appears in the above-identified patent and that said Letters Patent is hereby corrected as shown below:

Claim 1, column 8, line 27, "and", first occurrence, should read -- said --.

Signed and Sealed this

Twenty-eighth Day of February 1984

[SEAL]

Attest:

GERALD J. MOSSINGHOFF

Attesting Officer

Commissioner of Patents and Trademarks